US011890295B2

(12) United States Patent
Kim et al.

(10) Patent No.: US 11,890,295 B2
(45) Date of Patent: Feb. 6, 2024

(54) HELICOBACTER PYLORI ERADICATION METHOD INCLUDING STEP FOR ORALLY ADMINISTERING COMPOSITION INCLUDING COMPLEX OF NON-ABSORBABLE ANTIBIOTIC AND CLAY MINERAL TO SUBJECT

(71) Applicant: KOREA INSTITUTE OF GEOSCIENCE AND MINERAL RESOURCES, Daejeon (KR)

(72) Inventors: Jae-Hwan Kim, Pohang-si (KR); Il-Mo Kang, Seoul (KR); Young-Goo Song, Seoul (KR); Ki-Min Roh, Daejeon (KR); Yun-Goo Song, Seoul (KR); Sung-Man Seo, Pohang-si (KR); Dae-Young Kim, Geumsan-gun (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 112 days.

(21) Appl. No.: 17/269,501

(22) PCT Filed: Jun. 24, 2019

(86) PCT No.: PCT/KR2019/007611
§ 371 (c)(1),
(2) Date: Feb. 18, 2021

(87) PCT Pub. No.: WO2020/045807
PCT Pub. Date: Mar. 5, 2020

(65) Prior Publication Data
US 2021/0196740 A1  Jul. 1, 2021

(30) Foreign Application Priority Data

Aug. 31, 2018 (KR) ........................ 10-2018-0103868
Jun. 20, 2019 (KR) ........................ 10-2019-0073709

(51) Int. Cl.
| | |
|---|---|
| *A61K 31/7048* | (2006.01) |
| *A61P 31/04* | (2006.01) |
| *A61K 9/00* | (2006.01) |
| *A61K 31/43* | (2006.01) |
| *A61K 31/4439* | (2006.01) |
| *A61K 47/46* | (2006.01) |

(52) U.S. Cl.
CPC ........ *A61K 31/7048* (2013.01); *A61K 9/0065* (2013.01); *A61K 31/43* (2013.01); *A61K 31/4439* (2013.01); *A61K 47/46* (2013.01); *A61P 31/04* (2018.01)

(58) Field of Classification Search
CPC .. A61K 31/7036; A61K 47/52; A61K 9/0053; A61P 31/04
USPC .................................................... 514/41, 29
See application file for complete search history.

(56) References Cited

FOREIGN PATENT DOCUMENTS

| | | |
|---|---|---|
| FR | 2 677 253 A | 12/1992 |
| JP | H06500571 A1 | 1/1994 |
| KR | 10-0257367 B1 | 5/2000 |
| KR | 10-0550839 B1 | 2/2006 |
| KR | 10-0630479 B1 | 10/2006 |
| KR | 10-1541876 B1 | 8/2015 |
| KR | 101541876 B1 * | 8/2015 |
| KR | 1020140168588 * | 8/2015 |
| KR | 10-2054341 B1 | 12/2019 |

OTHER PUBLICATIONS

Song et al.; KR 101541876 B1; Aug. 6, 2015 (Machine-English Translation).*
Tsujimae et al. (Digestion 2016:94:240-246).*
Jeong et al. Gentamicin-intercalated smectite as a new therapeutic option for Helicobacter pylori eradication. J Antimicrob Chemother 2018; 73: 1324-1329. (Year: 2018).*
Office Action for Japanese Patent Application No. 2021-506991 dated Feb. 22, 2022 and English translation, 11 pages.
Jeong, et al., "Gentamicin-intercalated smectite as a new therapeutic option for Helicobacter pylori eradication," Abstracts of the 11th International Symposium on Antimicrobial Agents and Resistance and the 3rd International Interscience Conference on Infection and Chemotherapy, vol. 50, Supplement 1, International Journal of Antimicrobial Agents, Bexco, Busan, Korea, Sep. 14-16, 2017, pp. S1-S176.
Jeong, et al., "Gentamicin-intercalated smectite as a new therapeutic option for Helicobacter pylori eradication," Journal of Antimirob Chemother, Published on Feb. 12, 2018, vol. 73, No. 5, pp. 1324-1329.
Lee, et al., "Validation of in vitro Activity of Aminoglycosides Against Recently Isolated Helicobacter pylori for Commercialization of Gentamicin-intercalated Smectite Hybrid as A New Therapeutic Agent," Open Forum Infectious Diseases, Abstracts of Poster, Nov. 2018, vol. 5, suppl. 1, p. S733.
Lee, et al., "Fecal microbiome changes after Helicobacter pylori eradication with Smectite-gentamicin hybrid in mouse model," 1 page, ISAAR & ICIC Sep. 14-16, 2017.
Kim, et al., "Guidelines for the Diagnosis and Treatment of Helicobacter pylori Infection in Korea," 2013 Revised Edition, Korean J Gastroenterol, vol. 62, No. 1, pp. 3-26, Jul. 2013.
Brenciaglia, et al., "Activity of Amoxicillin, Metronidazole, Bismuth Salicylate and Six Aminoglycosides against Helicobacter pylori," Journal of Chemotherapy, vol. 8, No. 1, pp. 52-54, 1996.
Turnidge, "Pharmacodynamics and dosing of aminoglycosides," Infect Dis Clin N Am, 17, pp. 503-528, (year 2003).

(Continued)

*Primary Examiner* — Yih-Horng Shiao
(74) *Attorney, Agent, or Firm* — Lewis Roca Rothgerber Christie LLP

(57) ABSTRACT

The present application relates to an orally administered pharmaceutical composition or kit for eradicating *Helicobacter pylori*, including a complex of a non-absorbable antibiotic and a clay mineral. The pharmaceutical composition and kit of the present invention may further include a β-lactam antibiotic and/or a gastric acid inhibitor.

4 Claims, 9 Drawing Sheets

Specification includes a Sequence Listing.

(56) References Cited

OTHER PUBLICATIONS

Kim, et al., "Identification of Mycobacterial Species by Comparative Sequence Analysis of the RNA Polymerase Gene (rpoB)," Journal of Clinical Microbiology, vol. 37, No. 6, Jun. 1999, pp. 1714-1720.

Kim, et al., "The Influence of Number of Gastroscopic Biopsy Specimens on Follow-up Campylobacter-Like Organism (CLO) Test," Korean J Gastroenterol, vol. 35, 2000, pp. 422-428.

Kundu, et al., "Cag Pathogenicity Island-independent Up-regulation of Matrix Metalloproteinases-9 and -2 Secretion and Expression in Mice by *Helicobacter pylori* Infection*," The Journal of Biological Chemistry vol. 281, No. 45, pp. 34651-34662, Nov. 10, 2006.

Moon, et al., "Usefulness of a *Helicobacter pylori* stool antigen test for diagnosing *H. pylori* infected C57BL/6 mice," Lab. Anim. Res., vol. 29, No. 1, 2013, pp. 27-32.

Lee, et al., "Absence of vertical transmission of *Helicobacter pylori* in an experimental murine model," J. Vet. Sci., vol. 7, No. 3, 2006, pp. 225-228.

Lee, et al., "Prevalence of *Helicobacter* Species in Feces of Dogs using Polymerase Chain Reaction Analysis," Lab. Anim. Res., vol. 23, No. 3, 2007, pp. 339-344.

Shao, et al., "Antibiotic resistance of *Helicobacter pylori* to 16 antibiotics in clinical patients," Journal of Clinical Laboratory Analysis. vol. 32, No. 4, May 2018, pp. 1-5.

Lee, et al., "Can Aminoglycosides Be Used as a New Treatment for *Helicobacter pylori*? In vitro Activity of Recently Isolated *Helicobacter pylori*," Infect. Chemother., vol. 51, No. 1, Mar. 2019, pp. 10-20.

Shao, Y. et al, "Antibiotic resistance of Helicobacter pylori to 16 antibiotics in clinical patients", J. Clin. Lab. Anal., electronic publish Oct. 6, 2017, vol. 32, thesis e22339, pp. 1-5.

2449_ Validation of in vitro activity of aminoglycosides against recently isolated Helicobacter ~ with English abstract, (Open Forum Infectious Diseases, vol. 5, Issue suppl_1, Nov. 2018, p. S733).

\* cited by examiner

[FIG. 1]
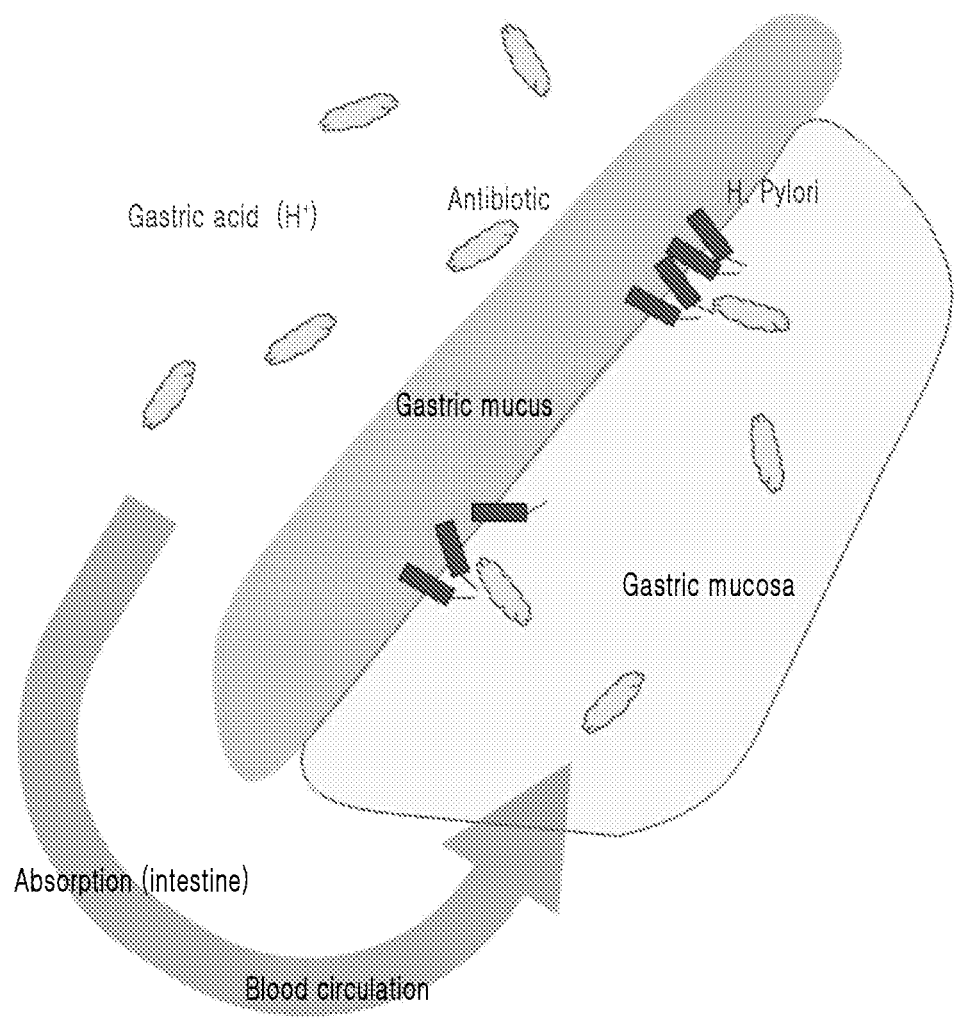

[FIG. 2]
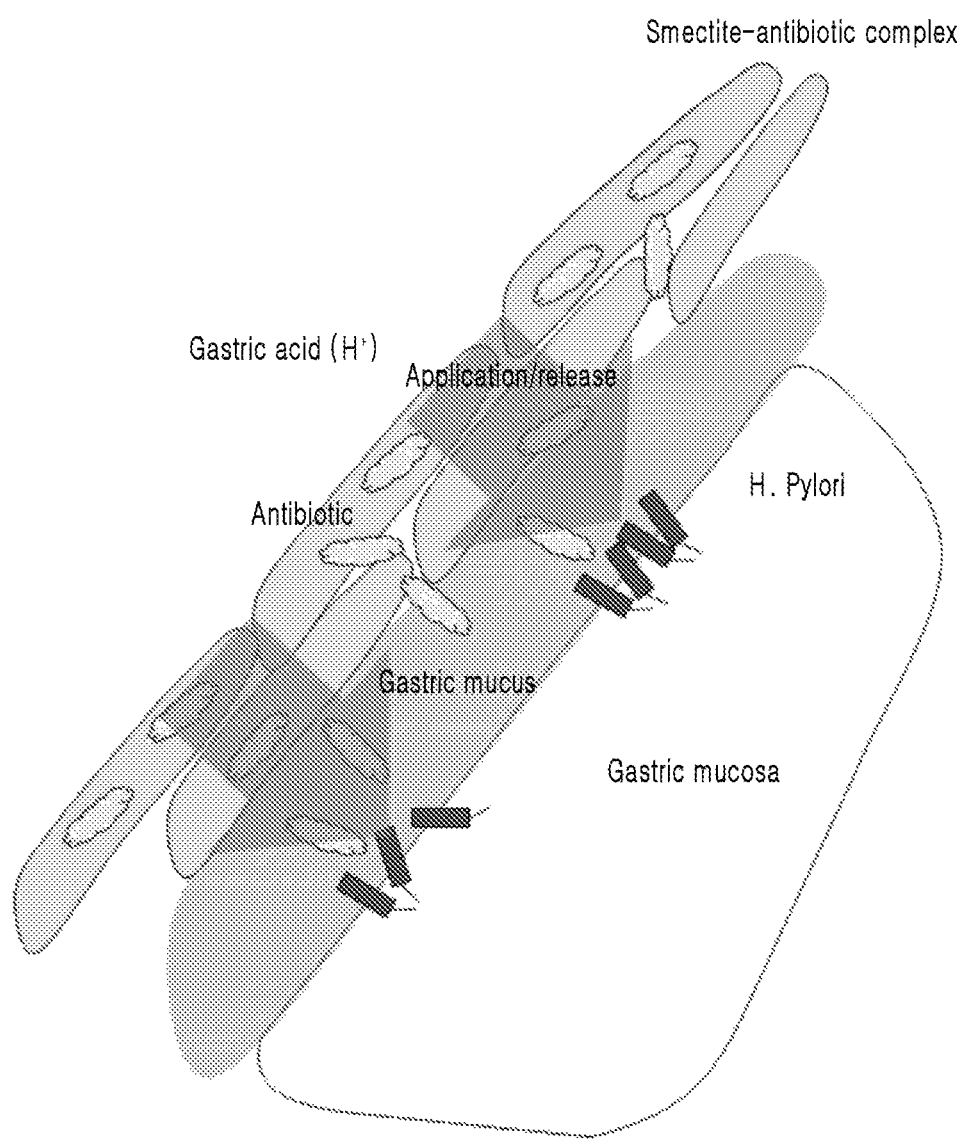

[FIG. 3]
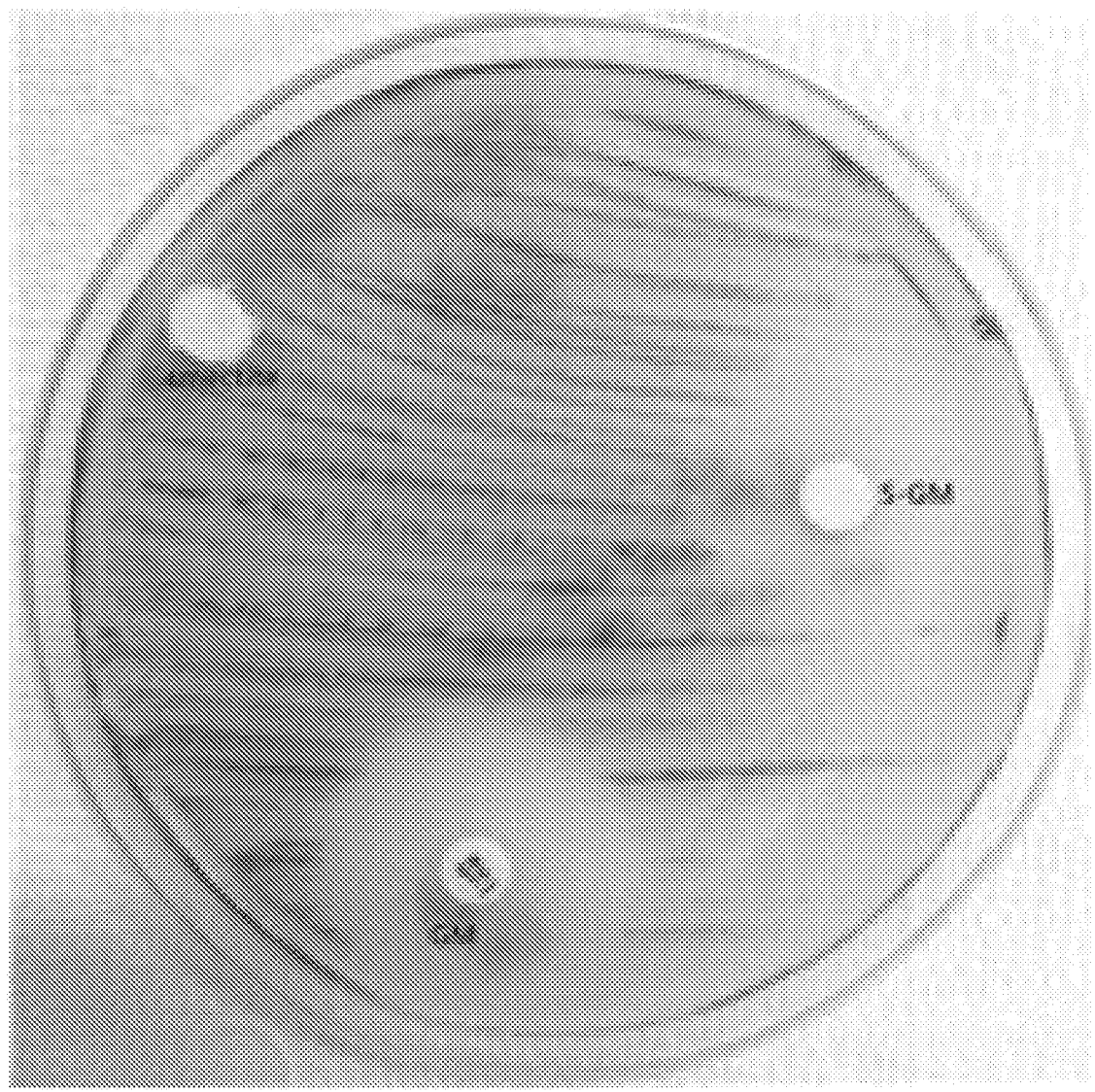

[FIG. 4]
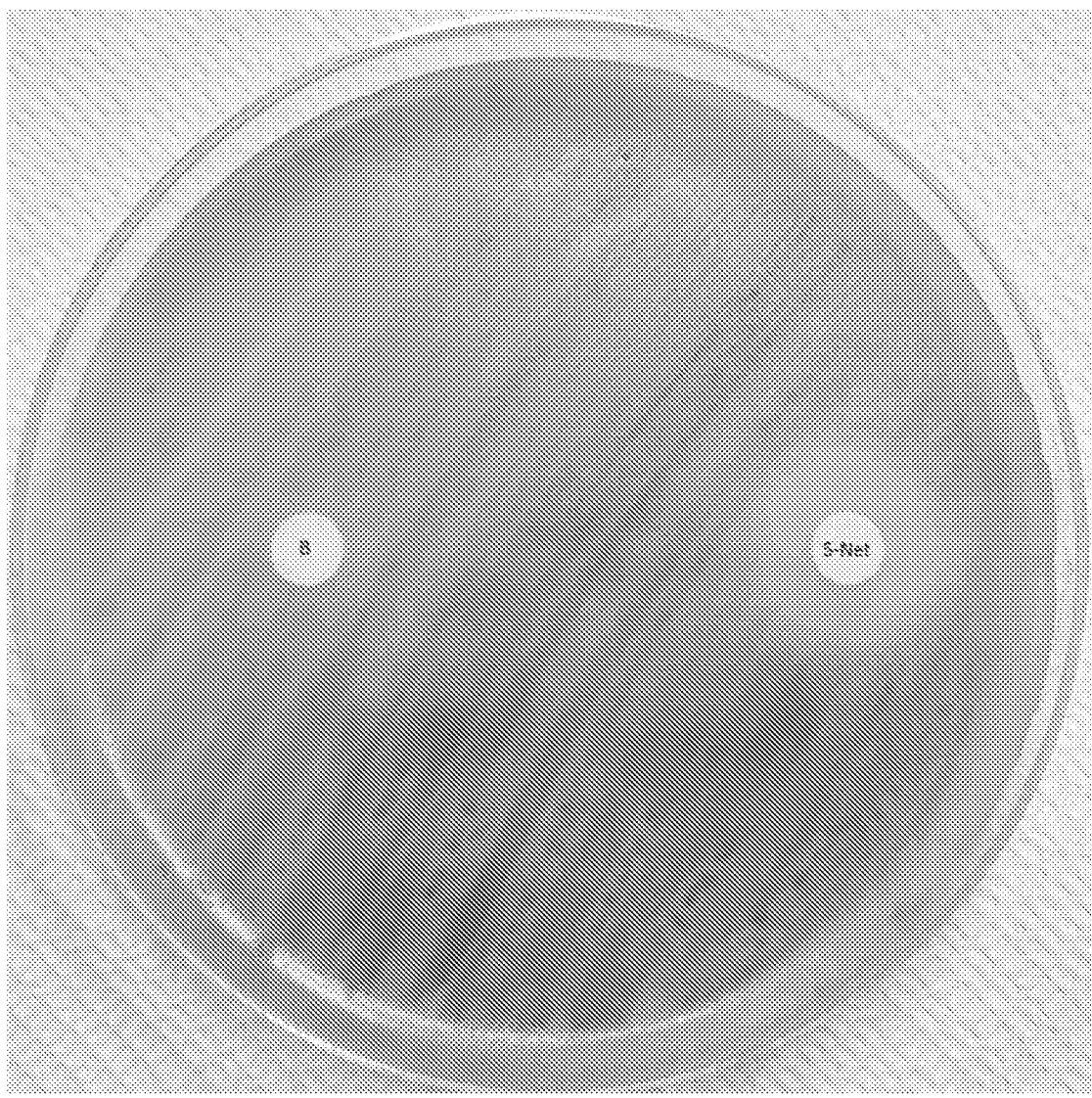

[FIG. 5]
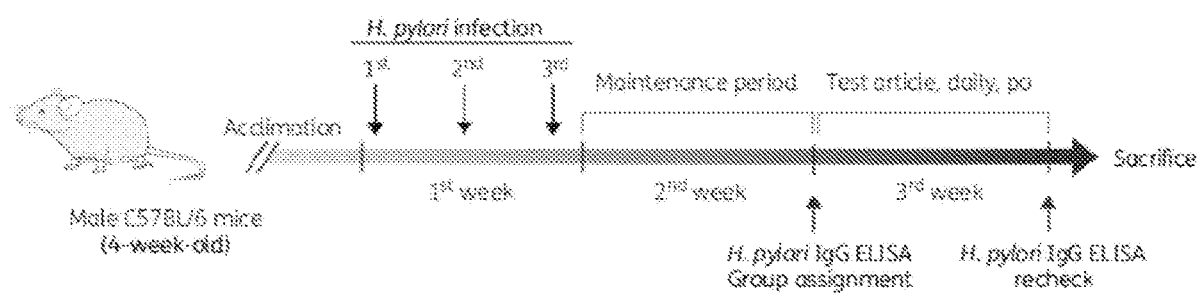

[FIG. 6]
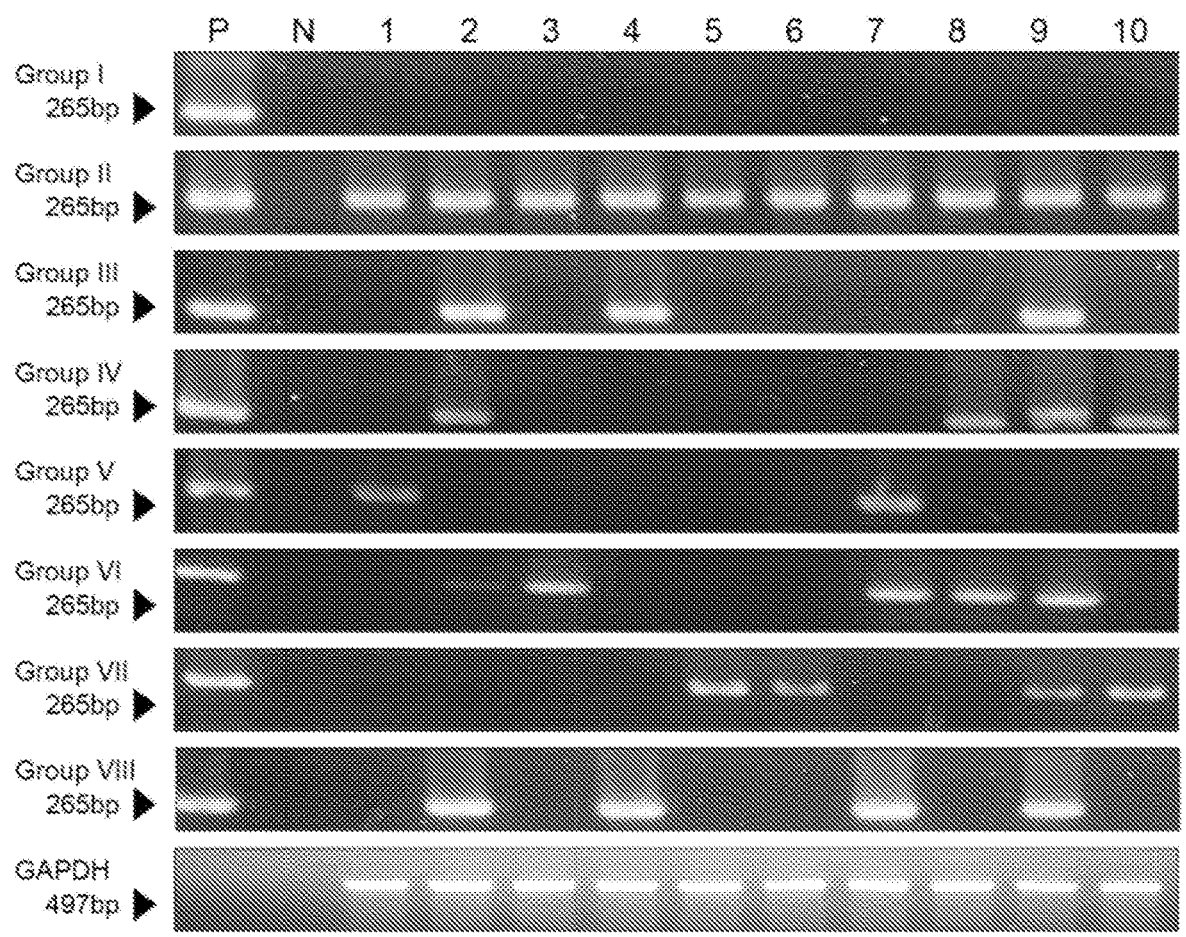

[FIG. 7]
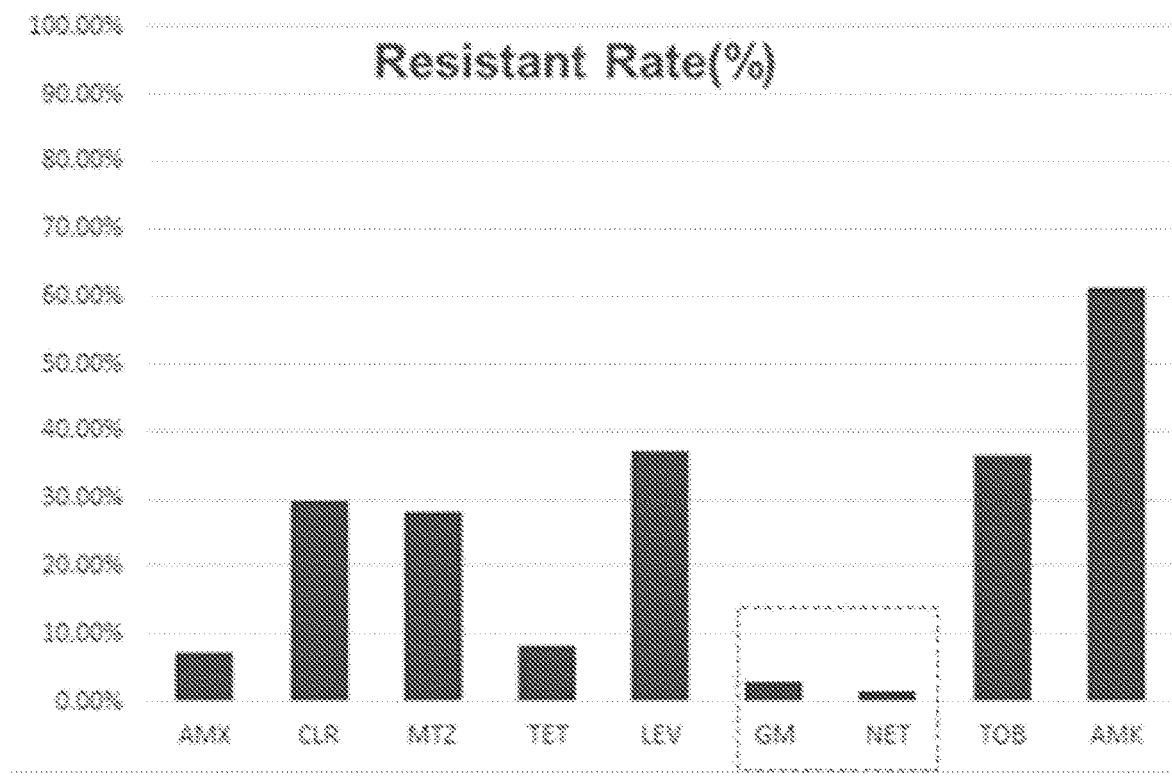

[FIG. 8a]
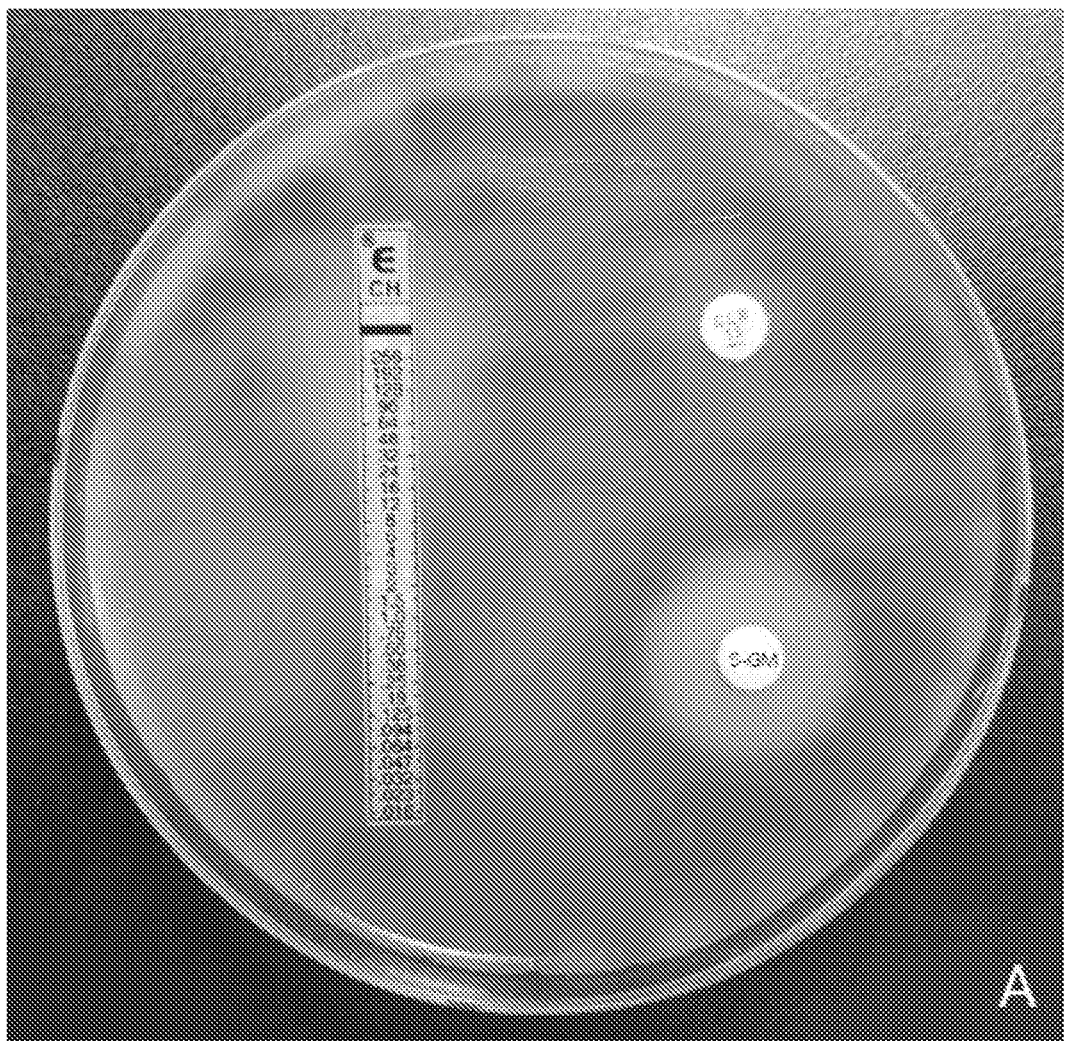

[FIG. 8b]
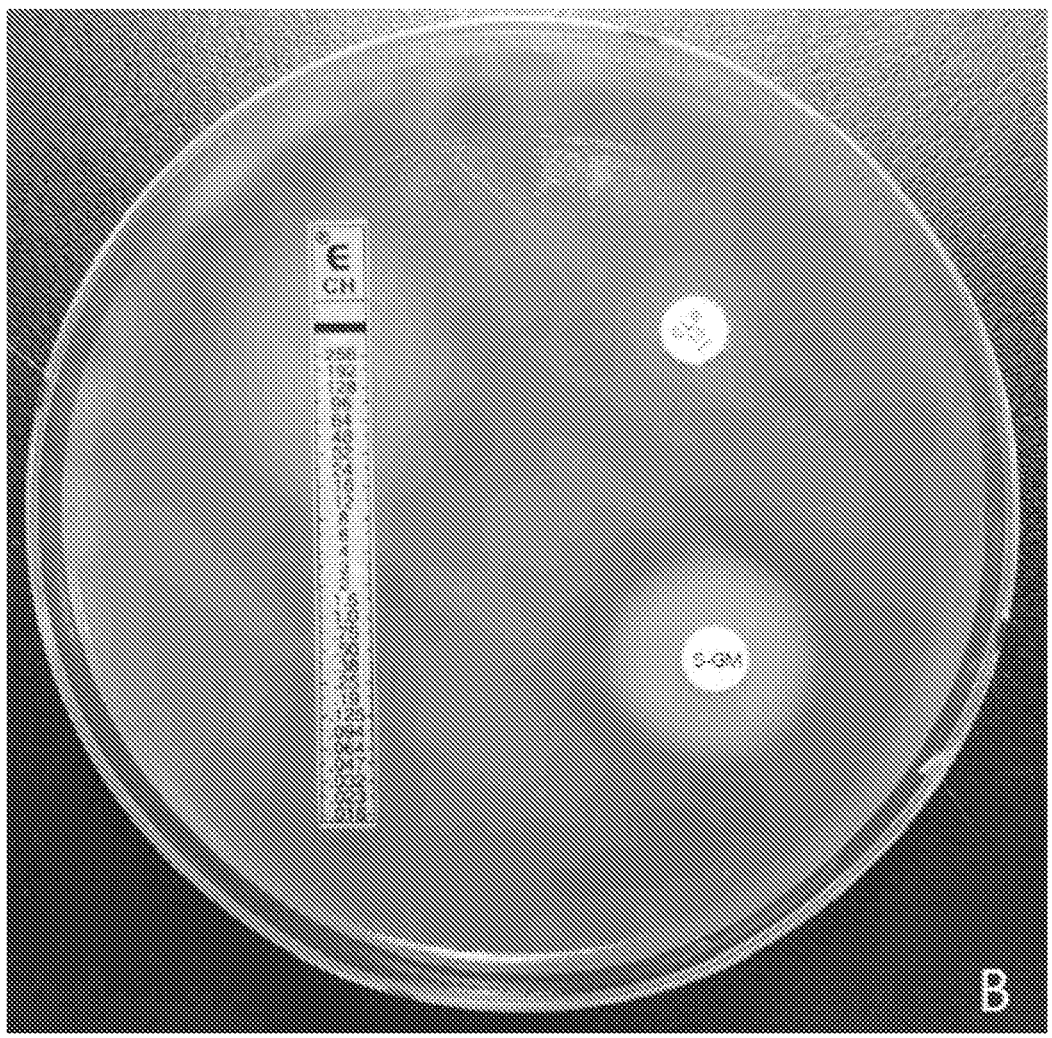

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: sense primer for amplification of ureA and ureC
      specific for H. pylori.
```

```
<400> SEQUENCE: 1
tgatgctcca ctacgctgga                                           20

<210> SEQ ID NO 2
<211> LENGTH: 20
<212> TYPE: DNA
<213> ORGANISM: Artificial
<220> FEATURE:
<223> OTHER INFORMATION: antisense primer for amplification of ureA and
      ureC specific for H. pylori.

<400> SEQUENCE: 2
gggtatgcac ggttacgagt                                           20

<210> SEQ ID NO 3
<211> LENGTH: 19
<212> TYPE: DNA
<213> ORGANISM: Artificial
<220> FEATURE:
<223> OTHER INFORMATION: sense primer for amplification of GAPDH

<400> SEQUENCE: 3
tggggtgatg ctggtgctg                                            19

<210> SEQ ID NO 4
<211> LENGTH: 21
<212> TYPE: DNA
<213> ORGANISM: Artificial
<220> FEATURE:
<223> OTHER INFORMATION: antisense primer for amplification of GAPDH

<400> SEQUENCE: 4
ggtttctcca ggcggcatgt c                                         21
```

HELICOBACTER PYLORI ERADICATION METHOD INCLUDING STEP FOR ORALLY ADMINISTERING COMPOSITION INCLUDING COMPLEX OF NON-ABSORBABLE ANTIBIOTIC AND CLAY MINERAL TO SUBJECT

CROSS-REFERENCE TO RELATED APPLICATION

This application is a U.S. National Phase Patent Application of International Application Number PCT/KR2019/007611, filed on Jun. 24, 2019, which claims priority of Korean Patent Application Number 10-2018-0103868, filed on Aug. 31, 2018 and Korean Patent Application Number 10-2019-0073709, filed on Jun. 20, 2019, the entire content of each of which is incorporated herein by reference.

INCORPORATION BY REFERENCE

The material in the text file entitled "SequenceListing.txt", originally filed with WIPO on Mar. 5, 2020 and being 1.27 bytes, is herein incorporated by reference in its entirety.

SEQUENCE LISTING

The instant application contains a Sequence Listing in ASCII format and the entire content of the electronic submission of the sequence listing is incorporated by reference in its entirety for all purposes. The ASCII file is named "201924_LOP190011PCTUS_patentin3.2_sequences.ST25.txt," was last modified on Oct. 20, 2023, and is 1,252 bytes in size.

TECHNICAL FIELD

The present invention relates to a method for eradicating *Helicobacter pylori*, including a step of orally administering a composition including a complex of a non-absorbable antibiotic and a clay mineral to a subject. Further, the present invention relates to a method for eradicating *Helicobacter pylori*, including a step of orally administering a complex of a non-absorbable antibiotic and a clay mineral to a subject. Further, the present invention relates to a method for preventing or treating gastrointestinal diseases caused by *Helicobacter pylori* bacteria, including a step of orally administering a composition including a complex of a non-absorbable antibiotic and a clay mineral to a subject. Further, the present invention relates to a method for preventing or treating gastrointestinal diseases caused by *Helicobacter pylori* bacteria, including a step of orally administering a complex of a non-absorbable antibiotic and a clay mineral to a subject. Further, the present invention relates to an orally administered pharmaceutical composition for eradicating *Helicobacter pylori*, including a complex of a non-absorbable antibiotic and a clay mineral. Further, the present invention relates to an orally administered kit for eradicating *Helicobacter pylori*, including a complex of a non-absorbable antibiotic and a clay mineral.

BACKGROUND ART

*H. pylori* is a gram-negative microaerobic spiral *bacillus* that affects the gastric mucosa and may be found by adhering to epithelial cells of the human stomach. Drug-resistant *H. pylori* strains are the most common cause of treatment failure. About 50% of the world's population is *H. pylori* positive, developing countries have a prevalence rate of 80% to 90% and developed countries have a prevalence rate of 35% to 40%. Since the first recommendation on *H. pylori* eradication treatment in Korea was published in 1998, a standard triple therapy which has been recommended as a first-line therapy until now is an administration method by combining clarithromycin, amoxicillin, and a gastric acid inhibitor. The eradicating effect of this standard triple therapy is currently showing a very low effect of about 70%, but no superior therapy to the conventional triple therapy is yet developed, and thus, despite the low eradicating effect, the triple therapy has been recommended as a first-line therapy (Korean J Gastroenterol 2013; 62:3-26). As described above, conventional therapies, including the standard triple therapy, are subjected to a process of eradicating *H. pylori* in which an orally administered antibiotic is dissolved in the stomach, absorbed in the intestine, moved through blood vessels, and finally released into the gastric mucosa (FIG. 1). However, this is because the administered antibiotic is absorbed in the intestine and then released into the gastric mucosa to have an eradicating effect, so that the antibiotic is systemically exposed, and there are a risk of side effects and the burden on a patient caused by the antibiotic.

Smectite is a phyllosilicate mineral in which two octahedral sheets consisting of Al, Mg, and Fe are combined with a tetrahedral sheet consisting of Si, Al, and Fe in a sandwich-shape from the top and bottom to form one unit layer (2:1 layer). The smectite unit layer has a negative charge, which is generated when tetrahedral Si having a positive tetravalent charge is isomorphic-substituted with Al or Fe having a positive trivalent charge, or octahedral Al or Fe' having a positive trivalent charge is isomorphic-substituted with Mg or Fe' having a positive divalent charge. Cations are induced between the unit layer and the unit layer through the negative charge generated in the unit layer, which means that smectite may be used as a drug carrier. Therefore, the use of smectite as a drug delivery vehicle has recently attracted great interest, and several studies have reported drug-inserted smectite hybrids of donepezil, lincomycin, chlorhexidine acetate, tetracycline, etc. for controlled delivery and release.

Aminoglycoside-based antibiotics are representative antibiotics used for the treatment of gram-negative bacteria, but have no oral drug, and are usable as only injections, and thus, have not been used in *H. pylori* eradicating treatment. In some studies, it was confirmed that a low minimum inhibitory concentration was maintained in the evaluation of in vitro activity of aminoglycoside against *H. pylori*. The most active aminoglycosides of the tested aminoglycosides were gentamicin, tobramycin and netilmicin, which have MIC90 and MIC50 values of 0.25 to 0.5 and 0.125 to 1.00 mg/L, respectively (Brenciaglia M I, Fornara A M, Scaltrito M M et al. Activity of amoxicillin, metronidazole, bismuth salicylate and six aminoglycosides against *Helicobacter pylori*. JChemother 1996; 8: 52-4). However, since the aminoglycosides are hardly absorbed in the gastrointestinal tract when administered orally, the aminoglycosides have been used only parenterally until now (Turnidge J. Pharmacodynamics and dosing of aminoglycosides. Infect Dis Clin North Am 2003; 17: 503-28). In addition, in actual in vivo evaluation, it has not been reported that aminoglycoside-based antibiotics have an effect of eradicating *H. pylori*.

Therefore, the present inventors have studied an *H. pylori* eradicating agent of effectively eradicating *H. pylori* in the gastrointestinal tract after oral administration, found that a composition for eradicating *H. pylori* of the present invention was not absorbed in the intestine and released from the stomach through blood vessels, but was orally administered and then an antibiotic reaching the stomach through the esophagus adhered to the gastric mucous layer to effectively eradicating *H. pylori*, and completed the present invention.

DISCLOSURE

Technical Problem

An object of the present invention is to provide a composition for eradicating *H. pylori* which is orally administered and then applied and acting to the gastric mucosa, a method for eradicating *H. pylori* using the same, and a method for preventing and treating gastrointestinal diseases caused by *H. pylori*.

Technical Solution

In order to achieve the object, the present invention provides a method for eradicating *Helicobacter pylori*, including a step of orally administering a composition including a complex of a non-absorbable antibiotic and a clay mineral to a subject. Further, the present invention provides a method for eradicating *Helicobacter pylori*, including a step of orally administering a complex of a non-absorbable antibiotic and a clay mineral to a subject. Further, the present invention provides a method for preventing or treating gastrointestinal diseases caused by *Helicobacter pylori* bacteria, including a step of orally administering a composition including a complex of a non-absorbable antibiotic and a clay mineral to a subject. Further, the present invention provides a method for preventing or treating gastrointestinal diseases caused by *Helicobacter pylori* bacteria, including a step of orally administering a complex of a non-absorbable antibiotic and a clay mineral to a subject. Further, the present invention provides an orally administered pharmaceutical composition for eradicating *Helicobacter pylori*, including a complex of a non-absorbable antibiotic and a clay mineral. Further, the present invention provides an orally administered kit for eradicating *Helicobacter pylori*, including a complex of a non-absorbable antibiotic and a clay mineral.

Advantageous Effects

According to the present invention, the pharmaceutical composition and kit includes a plate-like clay carrier to be applied to the gastric mucosa and enable targeted treatment on the gastric mucosa. In addition, there is an advantage of reducing the destruction of antibiotics in a gastric environment with low acidity and minimizing an effect on the intestinal bacteria.

DESCRIPTION OF DRAWINGS

FIG. 1 illustrates a process of eradicating *H. pylori* by a conventional triple therapy.

FIG. 2 illustrates a process of eradicating *H. pylori* by a complex of a non-absorbable antibiotic and a clay mineral of the present invention.

FIG. 3 illustrates a *Helicobacter pylori* eradication activity of a gentamicin-smectite complex (S-GEN). Top left disk: Smectite, Top right disk: S-GEN, Bottom disk: Gentamicin.

FIG. 4 illustrates a *Helicobacter pylori* eradication activity of a netilmicin-smectite complex (S-NET). Left disk: Smectite, Right disk: S-NET FIG. 5 illustrates a protocol for confirming the efficacy of anti-*H. pylori* in vivo. The protocol includes inoculation, the development of infection, and treatment of *H. pylori* in C57BL/6 mice.

FIG. 6 illustrates gastric mucosal tissues and PCR results after a study on a therapeutic effect of *H. pylori* infection using Groups 1 to 8.

FIG. 7 illustrates resistant rates of *H. pylori* to antibiotics.

FIG. 8a illustrates a result of comparing in vitro antibacterial effects of a CLR disk and an S-GM disk in a clarithromycin-resistant strain.

FIG. 8b illustrates a result of comparing in vitro antibacterial effects of a CLR disk and an S-GM disk in a clarithromycin-resistant strain.

BEST MODE FOR THE INVENTION

The present invention relates to a method for eradicating *Helicobacter pylori*, including a step of orally administering a composition including a complex of a non-absorbable antibiotic and a clay mineral to a subject.

Further, the present invention relates to a method for eradicating *Helicobacter pylori*, including a step of orally administering a complex of a non-absorbable antibiotic and a clay mineral to a subject.

Further, the present invention relates to a method for preventing or treating gastrointestinal diseases caused by *Helicobacter pylori* bacteria, including a step of orally administering a composition including a complex of a non-absorbable antibiotic and a clay mineral to a subject.

Further, the present invention relates to a method for preventing or treating gastrointestinal diseases caused by *Helicobacter pylori* bacteria, including a step of orally administering a complex of a non-absorbable antibiotic and a clay mineral to a subject.

Further, the present invention relates to an orally administered pharmaceutical composition for eradicating *Helicobacter pylori*, including a complex of a non-absorbable antibiotic and a clay mineral.

Further, the present invention relates to an orally administered pharmaceutical composition for eradicating antibiotic-resistant *Helicobacter pylori*, including a complex of a non-absorbable antibiotic and a clay mineral.

Further, the present invention relates to the use of an orally administered pharmaceutical composition for eradicating *Helicobacter pylori*, including a complex of a non-absorbable antibiotic and a clay mineral.

Further, the present invention relates to the use of an orally administered pharmaceutical composition for eradicating antibiotic-resistant *Helicobacter pylori*, including a complex of a non-absorbable antibiotic and a clay mineral.

Further, the present invention relates to an orally administered kit for eradicating *Helicobacter pylori*, including a complex of a non-absorbable antibiotic and a clay mineral.

Further, the present invention relates to an orally administered kit for eradicating antibiotic-resistant *Helicobacter pylori*, including a complex of a non-absorbable antibiotic and a clay mineral.

Further, the present invention relates to a method for eradicating *Helicobacter pylori*, including a step of administering a pharmaceutical composition of the present invention to a subject.

Further, the present invention relates to a method for eradicating antibiotic-resistant *Helicobacter pylori*, including a step of administering a pharmaceutical composition of the present invention to a subject.

Further, the present invention relates to a method for preventing or treating diseases caused by antibiotic-resistant *Helicobacter pylori*, including a step of administering a pharmaceutical composition of the present invention to a subject.

Hereinafter, the present invention will be described in detail.

Non-Absorbable Antibiotic

The non-absorbable antibiotic of the present invention is administered orally in the form of a complex with a clay mineral, and then applied to the gastric mucosa when reaching the stomach through the esophagus. The antibiotic is released from the complex applied to the gastric mucosa to eradicate *H. pylori*.

When the non-absorbable antibiotic of the present invention is not used for eradicating *H. pylori* in the stomach after the complex is orally administered, the non-absorbable antibiotic is not absorbed but excreted, thereby reducing the side effects of the antibiotic and the burden on the patient. In addition, in this case, since the non-absorbable antibiotic of the present invention is in the form of the complex combined with the clay mineral, the effect on the intestinal bacteria is low, and the destruction of the antibiotic is minimized in a gastric acid condition.

The non-absorbable antibiotic of the present invention is not particularly limited, but may be an aminoglycoside-based compound.

The aminoglycoside-based compound of the present invention may include gentamicin, tobramycin, amikacin, neomycin, netilmicin, and the like, preferably gentamicin.

Clay Mineral

In general, clay minerals have a layered structure in which crystal units formed by combining a silica sheet and an alumina sheet are stacked, that is, a plate-like structure. Among these clay minerals, in a clay mineral having interlayer expandability, since there is no hydrogen bond between the crystal units, the bonding strength between the crystal units is weak, and thus, if moisture is introduced between these crystal units, the clay mineral may be expanded. Therefore, even ions having a relatively large size may be easily introduced between crystal units of the clay mineral having interlayer expandability. Meanwhile, in the clay mineral having interlayer expandability, a negative layer charge is generated when tetrahedral Si having a positive tetravalent charge is isomorphic-substituted with Al or Fe having a positive trivalent charge, or octahedral Al or $Fe^{3+}$ having a positive trivalent charge is isomorphic-substituted with Mg or $Fe^{2+}$ having a positive divalent charge. However, cations such as calcium ions ($Ca^{2+}$), magnesium ions ($Mg^{2+}$), sodium ions ($Na^+$), and potassium ions ($K^+$) are combined between the layers or on the surface to have electrical neutrality as a whole.

The clay mineral of the present invention is a clay mineral that has a plate-like structure, specifically, interlayer expandability, and may be used as a carrier by inserting an antibiotic thereinto. The clay mineral of the present invention may be a smectite-based mineral, for example, montmorillonite or bentonite, beidellite, nontronite, saponite, hectorite, etc.

Complex of Non-Absorbable Antibiotic and Clay Mineral

In the complex of the non-absorbable antibiotic and the clay mineral of the present invention, the clay mineral is used as a transmitter, that is, a carrier that delivers the non-absorbable antibiotic to a gastric mucous layer. The complex has a structure in which the non-absorbable antibiotic is inserted into the clay mineral. The complex of the non-absorbable antibiotic and the clay mineral is administered orally, reaches the stomach through the esophagus, and then adheres to the gastric mucus layer to release the antibiotic (FIG. 2). That is, the eradicating is not performed by a process in which the complex of the present invention is administered orally and reaches the stomach through the esophagus, and then the antibiotic is dissolved in the stomach, and the dissolved antibiotic is moved to the intestine, absorbed in the intestine, moved along the blood vessels, and released into the gastric mucosa to eradicate *H. pylori*.

Since the clay mineral of the present invention has a plate-like structure, the clay mineral may be applied to the gastric mucous layer (mucosa) and has excellent drug loading ability, so that targeted treatment is enabled on the gastric mucous layer. In addition, it is possible to effectively maintain a minimum inhibitory concentration (MIC) on an affected area, thereby reducing the patient's burden on the antibiotic.

The complex of the non-absorbable antibiotic and the clay mineral of the present invention may be prepared using a general method disclosed in the art. A method of preparing a complex obtained by combining the clay mineral and a medicine has been disclosed through a plurality of papers so far, and those skilled in the art may properly use the method to prepare the complex of the present invention. For example, the complex of the non-absorbable antibiotic and the clay mineral of the present invention may be prepared by a method of Korean Patent Registration No. 10-1541876, in which the entire thereof is incorporated by reference in the present invention. In this case, the complex of the present invention may be prepared by using the preparing method of the complex, including the steps of supplying a dispersion solution of clay mineral microparticles having an expandable lattice structure and an antibiotic solution to a first space and a second space separated from each other by an ion exchange membrane, respectively, and maintaining the solutions for a first time; and removing the antibiotic solution from the second space and then supplying an antibiotic ion washing solution to the second space.

β-Lactam Antibiotic

The complex of the non-absorbable antibiotic and the clay mineral of the present invention may be administered to a subject together with a β-lactam antibiotic and/or a gastric acid inhibitor. Therefore, the pharmaceutical composition and kit of the present invention may further include a β-lactam antibiotic and a gastric acid inhibitor in addition to the complex of the non-absorbable antibiotic and the clay mineral.

The β-lactam antibiotic may be penicillin, methicillin, ampicillin, amoxicillin, cephalosporin, carbapenem, and the like, preferably amoxicillin.

Gastric Acid Inhibitor

The complex of the non-absorbable antibiotic and the clay mineral of the present invention may be administered to a subject together with a β-lactam antibiotic and/or a gastric acid inhibitor. The gastric acid inhibitor of the present invention is a proton pump inhibitor. The gastric acid inhibitor of the present invention may use a general gastric acid inhibitor and is not particularly limited. For example, the gastric acid inhibitor of the present invention may include omeprazole, esomeprazole, rabeprazole, lansoprazole, pantoprazole, or the like. When the subject using the pharmaceutical composition or kit of the present invention has weak stomach or excessive gastric acid secretion, the gastric acid inhibitor may be administered in combination with the complex of the non-absorbable antibiotic and the clay mineral.

Kit

The kit of the present invention includes the complex of the non-absorbable antibiotic and the clay mineral. Preferably, the kit of the present invention further includes a β-lactam antibiotic and/or a gastric acid inhibitor. The kit of the present invention is an orally administered kit for eradicating *H. pylori*.

Pharmaceutical Composition

The composition of the present invention may be a pharmaceutical composition, and the terms "composition" and "pharmaceutical composition" herein may be used interchangeably. The pharmaceutical composition of the present invention includes the complex of the non-absorbable antibiotic and the clay mineral. Preferably, the pharmaceutical composition of the present invention further includes a β-lactam antibiotic and/or a gastric acid inhibitor.

The complex of the non-absorbable antibiotic and the clay mineral of the pharmaceutical composition of the present invention is administered orally, reaches the stomach through the esophagus, and then adheres to the gastric mucous layer of the stomach to release the antibiotic. The pharmaceutical composition has a urease inhibitory activity, and may be a pharmaceutical composition for preventing or treating gastrointestinal diseases caused by *Helicobacter pylori* bacteria.

The pharmaceutical composition of the present invention may be a pharmaceutical composition for preventing, alleviating or treating diseases caused by *H. pylori*. The disease caused by *Helicobacter pylori* may be gastrointestinal damage, gastritis, gastric ulcer, duodenal ulcer, gastritis, gastric cancer, or MALT lymphoma.

The pharmaceutical composition of the present invention may include the complex of the non-absorbable antibiotic and the clay mineral, the β-lactam antibiotic and/or the gastric acid inhibitor in an amount of 0.01 to 80 wt %, preferably 0.02 to 65 wt %. However, the amount thereof may be increased or decreased according to the needs of a user, and may be appropriately increased or decreased depending on a situation such as age, diet, a nutritional status, and disease progression. In the pharmaceutical composition of the present invention, a ratio, that is, a composition of the complex of the non-absorbable antibiotic and the clay mineral, the β-lactam antibiotic and/or the gastric acid inhibitor may be appropriately determined by those skilled in the art.

The pharmaceutical composition of the present invention can be administered orally and may be used in the form of a general pharmaceutical formulation. Preferred pharmaceutical formulations include orally administered formulations such as tablets, hard or soft capsules, solutions, suspensions, syrups, and chewing tablets, and these pharmaceutical formulations may be prepared by using a conventional pharmaceutically acceptable carrier, for example, an excipient, a binder, a disintegrant, a lubricant, a solubilizing agent, a suspending agent, a preservative, an extender, or the like in the case of the orally administered formulations.

A dose of the pharmaceutical composition of the present invention may be determined by an expert according to various factors such as patient's condition, age, sex, and complications, but generally, the pharmaceutical composition may be administered in a dose of 0.1 mg to 10 g per 1 kg of an adult, preferably in a dose of 10 mg to 5 g. In addition, a daily dose of the pharmaceutical composition or a dose of ½, ⅓ or ¼ thereof is contained per unit dosage form, and may be administered 1 to 6 times a day. However, in the case of long-term intake for the purpose of health and hygiene or health regulation, the dose may be equal to or lower than the above range, and may be appropriately adjusted by a doctor in charge.

Disease Caused by *Helicobacter pylori*

The pharmaceutical composition and kit of the present invention may be used for the prevention, alleviation or treatment of diseases caused by *Helicobacter pylori*. The disease caused by *Helicobacter pylori* may be gastrointestinal damage, gastritis, gastric ulcer, duodenal ulcer, gastritis, gastric cancer, or MALT lymphoma. The *Helicobacter pylori* may be common *Helicobacter pylori*, and may be antibiotic-resistant *Helicobacter pylori*. At this time, the antibiotic-resistant *Helicobacter pylori* may be clarithromycin-resistant *Helicobacter pylori*. The pharmaceutical composition and kit of the present invention have an eradication activity on clarithromycin-resistant *Helicobacter pylori*.

Treatment Method or Eradication Method

The present invention relates to a method for eradicating *H. pylori*, including a step of orally administering the pharmaceutical composition of the present invention to a subject. Further, the present invention relates to a method for eradicating antibiotic-resistant *H. pylori*, including a step of orally administering the pharmaceutical composition of the present invention to a subject. The present invention relates to a method for preventing, alleviating or treating diseases caused by *H. pylori*, including a step of orally administering the pharmaceutical composition of the present invention to a subject. Further, the present invention relates to a method for preventing, alleviating or treating diseases caused by antibiotic-resistant *H. pylori*, including a step of orally administering the pharmaceutical composition of the present invention to a subject.

The subject may be a mammal diagnosed to be infected with *H. pylori*, or susceptible to *H. pylori* infection. Further, the subject may be a mammal diagnosed as being infected with antibiotic-resistant *H. pylori*, or susceptible to antibiotic-resistant *H. pylori* infection. The mammal may or may not include a human. Therefore, the treatment method of the present invention may treat a subject that has been infected with antibiotic-resistant *H. pylori*, or is susceptible to be infected with antibiotic-resistant *H. pylori*, and thus, has a treating subject range wider than that of conventional *H. pylori* eradicating drugs. In addition, the eradicating method of the present invention may eradicate antibiotic-resistant *H. pylori*, and thus, has an eradicating subject range of wider than that of conventional *H. pylori* eradicating drugs.

Antibiotic-Resistant *Helicobacter pylori*

The complex of the non-absorbable antibiotic and the clay mineral of the present invention, or the pharmaceutical composition including the complex has an eradication activity on antibiotic-resistant *Helicobacter pylori*. The antibiotic-resistant *Helicobacter pylori* may be clarithromycin-resistant *Helicobacter pylori*. For example, the antibiotic-resistant *Helicobacter pylori* may be *Helicobacter pylori* having a single resistance to clarithromycin, or may be *Helicobacter pylori* having a multiple resistance to a plurality of antibiotics, such as having a resistance to both clarithromycin and metronidazole at the same time or having at least one antibiotic selected from metronidazole, tetracycline, levofloxacin, and the like in addition to clarithromycin. While the amoxicilin resistance is less than 10%, the resistance of *Helicobacter pylori* to clarithromycin has been on the rise in recent years, and a major cause of treatment failure for eradicating *H. pylori* is the clarithromycin resistance. Therefore, the complex of the non-absorbable antibiotic and the clay mineral of the present invention, or the pharmaceutical composition including the complex having the eradication activity on clarithromycin-resistant *Helico-*

*bacter pylori* is particularly useful for subjects who have failed to conventional eradicating treatment.

MODES FOR THE INVENTION

Advantages and features of the present invention, and methods for accomplishing the same will be more clearly understood with reference to embodiments to be described in detail below. However, the present invention is not limited to the embodiments set forth below, and will be embodied in various different forms. The present embodiments are just for rendering the disclosure of the present invention complete and are set forth to provide a complete understanding of the scope of the present invention to a person with ordinary skill in the technical field to which the present invention pertains, and the present invention will only be defined by the scope of the appended claims.

<Materials and Method>
<Experimental Ethics>

An animal test was performed on rats approved by the Institutional Animal Care and Use Committee of the National Center of Efficacy Evaluation for the Development of Health Products Targeting Digestive Disorders in Incheon, Korea. Mouse experiments were reviewed and approved by the Institutional Animal Care and Use Committee of Wonkwang University School of Medicine. Mice were treated according to the guidelines and controls for animal use and management of Wonkwang University in Iksan, Korea, and were optionally supplied with water and standard experimental diets.

<Statistical Analysis>

Data were expressed as mean±SD, and experimental groups were compared using a nonparametric Mann-Whitney-U test. 95% CIs were obtained for a detection rate using a MINITAB statistical software program (Minitab Inc., PA, USA). If 95% CIs of two values did not overlap with each other, the two values were considerably different from each other. P value<0.05 was considered statistically significant. The results were analyzed using Statistics Package for Social Science (SPSS 12.0 for Windows; SPSS Inc., Chicago, Ill., USA).

<Experimental Example 1> Eradication Activity of Antibiotic-Clay Mineral Complex <1-1> Insertion of Antibiotic A gentamicin solution (2 mg/mL) was prepared using United States Pharmacopeia (USP)-grade gentamicin sulfate produced by Bio Basic Inc.

Ca-smectite was prepared by purifying bentonite from Gyeongbuk, Korea. A gentamicin-smectite complex S-GEN (gentamicin-inserted smectite hybrid) was prepared by mixing 250 ml of a gentamicin solution per gram of Ca-smectite and stirring vigorously for 24 hours. In this specification, the term S-GEN (gentamicin-inserted smectite hybrid), as the gentamicin-smectite complex, was used interchangeably with the term S-GM. After mixing, the hybrid solution was dialyzed with 5 L of distilled water at 50° C. for 8 hours, which was repeated 3 or 4 times until no sulfate ions were detected with $PbCl_2$. Hybrid powder was obtained by freeze-drying the dialyzed hybrid solution for 2 to 3 days. The amount of gentamicin released from the hybrid was determined by a batch-release test, and at this time, 25 mL of a pH 1.2 solution was repeatedly added to the same 100 mg of the hybrid powder. The gentamicin concentration from a supernatant was determined using LC-MS. LC analyzes were performed using a Thermo Scientific ICS system. MS analysis was performed using electrospray ionization and a Thermo Scientific MSQ Plus single-quadrupole mass spectrometer. The total amount of gentamicin released within 1 hour was found to be to 5.0 mg per 100 mg of hybrid.

On the other hand, a netilmicin-smectite complex S-NET was prepared using netilmicin instead of gentamicin in the same manner.

<1-2> Evaluation of Eradication Activity In Vitro

The eradication activities of S-GEN and S-NET were evaluated. *Helicobacter pylori* bacteria were applied on a medium (red), and a sample was made in the form of a disk and placed on the medium to measure an eradicating effect. At this time, if the red color disappeared around the disk, it was meant that there was the eradicating effect.

As a result, it was confirmed that both the gentamicin-smectite complex (S-GEN) and the netilmicin-smectite complex (S-NET) had the eradication activity of *Helicobacter pylori* (FIGS. 3 and 4, in FIG. 3, Top left: Smectite, Top right: S-GEN, and Bottom: gentamicin; in FIG. 4, Left: smectite, and Right: S-NET).

<Experimental Example 2> Application of Gastric Mucosa in Rats 7-week-old male Sprague-Dawley rats (220 g±20% body weight) were purchased from Samtako Ltd. of Osan, Korea to test the application of the gastric mucosa. The rats were fasted for 24 hours before the experiment. Two groups of 10 rats were ingested with smectite or S-GEN at 10 mL/kg (150 mg/kg) and euthanized after 1 hour. For the analysis of the application efficiency of the gastric mucosa, the stomachs of the rats were excised and cut along the greater curvature, and pinned. The gastric distribution ratio was calculated according to Equation 1 below.

Gastric distribution ratio (%)={Gastric distribution area $(cm^2)$/total gastric area $(cm^2)$}×100  <Equation 1>

The ratio and the areas were analyzed using Leica Application Suite V4 (Leica Microsystems Ltd., Korea). The gastric distribution ratio was expressed as the mean (±standard deviation).

<Experimental Example 3> Efficacy of Anti-*H. pylori* In Vivo

<3-1> Inoculation of Experimental Animals 4-week-old male C57BL/6 mice were purchased from Japan SLC, Inc. of Shizuoka, Japan for evaluation of anti-*H. pylori*. The mice were 5 weeks old at the start of the experiment and weighed with 18 to 20 g. *H. pylori* SS1 was used for inoculation. The bacteria were cultured on a *Brucella* blood agar (Merck, Germany) at 37° C. for 72 hours under microaerobic conditions (10% $CO_2$, 85% $N_2$ and 5% $O_2$). For evaluation of anti-*H. pylori* in vivo, 80 mice were acclimated for 1 week before the experiment.

After the acclimation, the animals were fasted for 12 hours, and 70 mice were infected with 0.5 mL of a 2.0×10⁹ cfu/mL *H. pylori* suspension, and administered intragastrically with the *H. pylori* suspension via oral ingestion every 48 hours, 3 times per week. The day of inoculation was considered as day 0 and from 1 to 21 days thereafter. The uninfected group was used as a normal control group, and received equivalent volumes of PBS and distilled water.

<3-2> Treatment of Experimental Animals

Mice were divided into the following 8 groups by 10 mice, and rested for 1 week after the last inoculation:

Group 1: Normal group of uninfected mice.

Group 2: No-treated control group receiving distilled water.

Group 3: Treated with amoxicillin (14.25 mg/kg), clarithromycin (7.15 mg/kg) and a proton pump inhibitor (PPI, omeprazole was used in all groups receiving PPI at 400 µmol/kg) and used as a positive control group.

Group 4: Treated with amoxicillin (14.25 mg/kg), gentamicin (4 mg/kg) and PPI (400 µmol/kg).

Group 5: Treated with amoxicillin (14.25 mg/kg), S-GEN (78 mg/kg) and PPI (400 µmol/kg).

Group 6: Treated with gentamicin (4 mg/kg) and PPI (400 µmol/kg).

Group 7: Treated with S-GEN (78 mg/kg) and PPI (400 µmol/kg).

Group 8: Treated with amoxicillin (14.25 mg/kg) and PPI (400 µmol/kg).

The treatments were administered orally once a day for 7 consecutive days. In order to confirm the serological status of H. pylori in infected mice, the levels of H. pylori immunoglobulin G (IgG) were confirmed with an ELISA kit (Cusabio Biotech Co., USA) before treatment.

<Experimental Example 4> Confirmation of Bacteria

After 12 hours of the last administration, the mice were euthanized and the gastric tissues were extracted. The gastric mucosa from the pylorus was biopsied for a Campylobacter-like organism (CLO) test and PCR for H. pylori. Additionally, 0.5 g of feces per mouse were collected in the rectum and the colon, suspended in an equal volume of distilled water, and filtered for H. pylori antigen (Ag) detection and H. pylori PCR in feces.

<4-1> CLO Test

Gastric mucosa samples of the pylorus were analyzed with CLO kits (Asan Pharmaceutical Co., Seoul, Korea), and incubated at 37° C. for 12 hours to test an urease activity. Responses (color change) were considered as negative at light yellow or positive at dark red. Response scores were 0 to 3, wherein 0 represented no color change, 1 represented bright red, 2 represented bright purple, and 3 represented dark red.

<4-2>H. pylori PCR in Gastric Mucosa

H. pylori DNAs were prepared using a bead beater/phenol extraction method (Kim B-J, Lee S-H, LyuM-A et al. Identification of mycobacterial species by comparative sequence analysis of the RNA polymerase gene (rpoB). J Clin Microbiol 1999; 37: 1714-20). A bacterial suspension was placed in a 2.0 mL screw cap microcentrifuge tube filled with 200 µL of phenol, chloroform, and isoamyl alcohol (50:49:1) and 200 µL (paced volume) of glass beads (diameter, 0.1 mm; Biospec Products, Bartlesville, Okla., USA). The tube was vibrated with a mini-bead beater (Biospec Products) for 30 seconds and centrifuged for phase separation (12,000 g for 15 minutes). An aqueous phase was then transferred to another clean tube, and 10 µL of 3 M sodium acetate and 250 µL of ice-cold absolute ethanol were added. In order to precipitate the DNA, the mixture was kept at −20° C. for 10 minutes. The harvested DNA pellets were dissolved in 60 µL of a Tris-EDTA buffer (pH 8.0) and used as a template DNA for PCR. The PCR was performed using AccuPower PCR Premix (Bioneer, Daej eon, Korea). After an initial denaturation/activation step (95° C. for 5 minutes), DNA (50 ng) was amplified in a volume of 20 µL for 35 cycles of denaturation (94° C. for 60 seconds), annealing (62° C. for 60 seconds) and elongation (72° C. for 90 seconds) using the following primers: H. pylori-specific ureA and ureC, sense 50-TGATGCTCCACTACGCTGGA-30 (SEQ ID NO: 1) and antisense 50-GGGTATGCACGGT-TACGAGT-30 (SEQ ID NO: 2) (expected product of 265 bp) (Kim Y B, Kim S T, Lee S W et al. The influence of number of gastroscopic biopsy specimens on follow-up Campylobacter-like organism (CLO) test.Korean J Gastroenterol 2000; 35: 422-8), and GAPDH, sense 50-TGGGGT-GATGCTGGTGCTG-AG-30 (SEQ ID NO: 3) and antisense 50-GGTTTCTC CAGGCGGCATGTC-30 (SEQ ID NO: 4) (expected product of 497 bp) (Kundu P, Mukhopadhyay A K, Patra R et al. Cag pathogenicity is and independent up-regulation of matrix metalloproteinases-9 and -2 secretion and expression in mice by Helicobacter pylori infection. J Biol Chem 2006; 281:34651-62). PCR products were analyzed by electrophoresis on a 1.5% agarose gel.

<4-3> Detection of H. pylori Antigen in Mouse Feces

An H. pylori antigen was evaluated using a commercially available SD Bioline H. pylori Ag kit (Standard Diagnostics, Inc.) according to the manufacturer's instructions. Specimens (250 mg) were incubated with a diluted solution at room temperature for 30 minutes, and then 100 µL of the samples were placed in a H. pylori antigen test device. The results were checked after 15 minutes. As a result, a single red line indicated negative H. pylori and a double red line indicated positive H. pylori (Moon D-I, Shin E-H, Oh H-G et al. Usefulness of a Helicobacter pylori stool antigen test for diagnosing H. pylori infected C57BL/6 mice. Lab Anim Res 2013; 29: 27-32).

<4-4>H. pylori PCR in Mouse Feces

Genomic DNAs were extracted from fecal samples using an AccuPrep Stool DNA Extraction Kit (Bioneer, Daej eon, Korea) according to the manufacturer's instructions (Lee J-U, Jung K, Kim O. Absence of vertical transmission of Helicobacter pylori in an experimental murine model. JVetSci 2006; 7: 225-8). A set of primers of SEQ ID NOs: 1 and 2 was used to amplify H. pylori-specific ureA and ureC (265 bp) (Kim Y B, Kim S T, Lee S W et al. The influence of number of gastroscopic biopsy specimens on follow-up Campylobacter-like organism (CLO) test. Korean J Gastroenterol 2000; 35: 422-8). A template DNA (50 ng) and 20 pmol of each primer were added in a PCR mixture tube including 1 U of Taq DNA polymerase, 250 µM of each deoxynucleoside triphosphate, 50 mM Tris-HCl (pH 8.3), 40 mM KCl, 1.5 mM MgCl$_2$ and a gel loading dye. The volume was adjusted to 20 µL using distilled water. After initial denaturation at 95° C. for 5 minutes, the reaction mixture was added to 35 amplification cycles (60 seconds at 94° C., 60 seconds at 62° C., and 90 seconds at 72° C.), and then elongated at 72° C. for 10 minutes (GeneAmp 9700, Perkin Elmer, USA).

PCR products were electrophoresed on a 1.5% agarose gel (Lee H-A, Park Y-S, Kim O. Prevalence of Helicobacter species in feces of dogs using polymerase chain reaction analysis. Lab Anim Res 2007; 23:339-44).

<Experimental Example 5> Quantification of Inflammatory Cytokines

Plasma was obtained for IL-8 and TNF-α analysis on day 21 by insertion of a heparinized microhaematocrit tube into the ophthalmic venous plexus of the mice. The plasma IL-8 and TNF-α levels were measured using mouse ELISA kits (R&D Systems, Minneapolis, Minn., USA).

<Experimental Example 6> Efficacy of Anti-H. pylori In Vivo According to Treatment Condition of S-GEN <6-1> Inoculation of Experimental Animals Male C57BL/6 mice were purchased from Japan SLC, Inc. of Shizuoka, Japan for evaluation of anti-H. pylori.

4-week-old mice were acclimated and then infected with *H. pylori* SS1 three times for 1 week, kept for two weeks, and thereafter, a test substance was suspended according to a specified dose and administered orally at the same time every day by 10 ml per kg of mouse. At this time, the test substance was administered orally once a day for 7 days.

<6-2> Treatment of Experimental Animals

Mice were divided into the following 5 groups by 10 mice, and rested for 1 week after the last inoculation:

Normal control group: vehicle (no infection), PBS was administered. 10 mg/kg of distilled water was received.

Negative control group: vehicle (*H. pylori* infection), 10 mg/kg of distilled water was received.

Test group 1: (*H. pylori* infection) AMX (14.25 mg/kg/day), CLR (14.3 mg/kg/day), PPI (138 mg/kg/day)

Test group 2: (*H. pylori* infection) AMX (14.25 mg/kg/day), S-GM (202 mg/kg/day), PPI (138 mg/kg/day) (at this time, Gentamicin of 8 mg/kg)

Test group 3: (*H. pylori* infection) AMX (14.25 mg/kg/day), S-GM (101 mg/kg/day)

AMX: Amoxicillin
CLR: Clarithromycin
S-GM: Gentamicin-inserted smectite hybrid
PPI: Proton pump inhibitor <Experimental Example 7> Eradicating Effect of S-GM on Antibiotic-Resistant *H. pylori*

<7-1> Evaluation of Antibiotic Resistant Rate

In virto MIC for non-absorbable antibiotic candidates (gentamicin, netilmicin, tobramycin, and amikacin) to be used as novel therapeutic agents was measured by making complexes with antibiotics (amoxicillin, clarithromycin, metronidazole, levofloxacin, and tetracyclin) that were actually used for *Helicobacter* eradicating treatment in clinical trials and smectite, and MIC50 and MIC90 were identified. For this end, 187 culture-positive clinical strains obtained from 1,265 patient specimens were used.

<7-2> Evaluation of Eradication Activity In Vitro

The eradication activities of S-GM and clarithromycin were evaluated for a clarithromycin-resistant strain (CLR MIC: 48 mg/L). Clarithromycin-resistant *Helicobacter pylori* bacteria were applied on a medium (red), and a sample was made in the form of a disk and placed on the medium to measure an eradicating effect. At this time, if the red color disappeared around the disk, it means that there was the eradicating effect.

<Results>

Result of Experimental Example 2

Application of Gastric Mucus Layer in Rats

Experimental conditions of 10 mL/kg (150 mg/kg) were selected, and the experimental rats were euthanized after 1 hour of oral administration in consideration of a drug release time from the hybrid. S-GEN showed 60.2% (±14.3%) of an application rate.

Result of Experimental Example 3

Evaluation of Anti-*H. pylori* In Vivo

In order to evaluate the in vivo efficacy of S-GEN on *H. pylori*, an *H. pylori* infection model was made (FIG. 5). In addition, to confirm *pylori* infection, *H. pylori* IgG levels were confirmed before and after treatment (Table 1: Plasma concentration of *H. pylori* IgG in each group).

TABLE 1

| Group | Inoculation *H. pylori* infection | Treatment | N | Concentration of *H. pylori* IgG Before treatment | After treatment |
|---|---|---|---|---|---|
| Group 1 | No | Distilled water | 10 | 0.26 ± 0.01 | 0.26 ± 0.00** |
| Group 2 | Yes | Distilled water | 10 | 0.58 ± 0.05a* | 0.74 ± 0.01 |
| Group 3 | Yes | AMX + CLR + PPI | 10 | | 0.33 ± 0.01** |
| Group 4 | Yes | AMX + GEN + PPI | 10 | | 0.35 ± 0.01** |
| Group 5 | Yes | AMX + S-GEN + PPI | 10 | | 0.32 ± 0.01** |
| Group 6 | Yes | GEN + PPI | 10 | | 0.40 ± 0.01** |
| Group 7 | Yes | S-GEN + PPI | 10 | | 0.34 ± 0.01** |
| Group 8 | Yes | AMX + PPI | 10 | | 0.35 ± 0.01* |

AMX: Amoxicillin
CLR: Clarithromycin
GEN: Gentamicin
[a] Data are presented as the mean ± standard deviation of 70 infected mice (Groups 2 to 8).
*Substantially different from Group 1 (p <0.01)
**Substantially different from Group 2 (p <0.01)

Result of Experimental Example 4

*H. pylori* PCR and CLO Test of Gastric Mucosa

Repeated intragastric inoculation of *H. pylori* in mice made a positive response (red) in the CLO test of the gastric mucosa (Table 2: CLO test results with gastric mucosa after treatment).

TABLE 2

| Group[a] | Percentage of negative animal by CLO test (95% CI[b]) | CLO value |
|---|---|---|
| Group 1 | 100 (72.2-100.0) | 0.0 ± 10.0 |
| Group 2 | 0 (0.0-27.6) | 3.0 ± 0.0 |
| Group 3 | 70 (39.7-89.2)* | 0.9 ± 1.5* |
| Group 4 | 60 (31.2-83.1)* | 1.2 ± 1.6* |
| Group 5 | 80 (49.0-94.3)* | 0.6 ± 1.3* |
| 9 dnojg | 50 (23.7-78.3) | 1.5 ± 1.6 |
| Group 7 | 60 (31.2-83.1)* | 1.2 ± 1.6* |
| Group 8 | 60 (31.2-83.1)* | 1.2 ± 1.6* |

[a]Each group consisted of 10 mice.
[b]Incidence percentage (95% CI) was calculated with a MiniTab statistical program.
*Substantially different from Group 2 (p <0.05)

The cure rates of the gastric mucosa (100-positive responses) were 70%, 60%, 80%, 50%, 60% and 60% in Groups 3 to 8, respectively. The CLO score of Group 5 was the lowest among the *H. pylori* infected groups, and significantly lower than that of Group 2.

PCR products of *H. pylori*-specific ureA and ureC (265 bp) were electrophoresed on a 1.5% agarose gel and visualized (FIG. 6).

The cure rate was the same as those confirmed by the CLO test.

*H. pylori* Antigen and PCR in Mouse Feces

A fecal antigen kit was used to detect *H. pylori* in feces. Positive results in Group 2 and negative results in other groups continued to be observed.

*H. pylori* PCR was performed to evaluate the therapeutic effects in *H. pylori*-infected mice (Table 3: PCR analysis of *H. pylori* in feces after treatment). The cure rates were 90% and 100% in Group 3 (standard treatment) and Group 5 (treatment with amoxicillin/S-GEN/PPI), respectively.

TABLE 3

| Group[a] | Percentage of negative animals by PCR of feces (95% CI[b]) |
|---|---|
| Group 1 | 100 (72.2-100.0) |
| Group 2 | 0 (0-27.6) |
| Group 3 | 90 (60.0-98.2)* |
| Group 4 | 80 (49.0-94.3)* |
| Group 5 | 100 (72.2-100.0)* |
| Group 6 | 70 (39.7-89.2)* |
| Group 7 | 80 (49.0-94.3)* |
| Group 8 | 70 (39.7-89.2)* |

[a]Each group consisted of 10 mice.
[b]Incidence percentage (95% CI) was calculated with a MiniTab statistical program.
*Substantially different from Group 2 (p <0.05)

Result of Experimental Example 5
Quantification of Inflammatory Cytokines

To confirm an effect of anti-*H. pylori* containing S-GEN on the production of cytokines, plasma concentrations of inflammatory cytokines were measured in mice (Table 4). The levels of IL-8 and TNF-α in the treatment groups were significantly lower than those in Group 2 (Table 4: plasma concentrations of IL-8 and TNF-α). Plasma levels of IL-8 and TNF-α in Group 5 were the lowest among the treatment groups.

TABLE 4

| Group[a] | Concentration of IL-8 (µg/ml) | Concentration of TNF-α(µg/ml) |
|---|---|---|
| Group 1 | 3.73 ± 0.82* | 16.14 ± 4.99* |
| Group 2 | 7.71 ± 0.66 | 44.43 ± 8.23 |
| Group 3 | 4.12 ± 0.45* | 23.59 ± 0.48** |
| Group 4 | 3.98 ± 0.21* | 23.20 ± 2.52** |
| Group 5 | 3.57 ± 0.38* | 17.66 ± 3.21** |
| Group 6 | 4.24 ± 0.42* | 24.30 ± 1.84** |
| Group 7 | 4.08 ± 0.26* | 18.76 ± 1.33** |
| Group 8 | 4.52 ± 0.36* | 22.13 ± 3.59** |

Data were expressed as mean ± standard deviation for 10 mice per group (µg/ml)
[a]Each group consisted of 10 mice.
*Substantially different from Group 2 (p <0.05)
**Substantially different from Group 2 (p <0.01)

Result of Experimental Example 6

Experimental animals treated in Experimental Example 6 were shown in Table 5 below.

TABLE 5

| | Disease induction | Test substance | Dose (mg/kg) | Number of animals |
|---|---|---|---|---|
| Normal control group | PBS | Distilled water | 10 | 10 |
| Negative control group | *H. pylori* | Distilled water | 10 | 10 |
| Test group 1 | | AMX + CLR + PPI | 10 | 10 |
| Test group 2 | | AMX + S-GM + PPI | 10 | 10 |
| Test group 3 | | AMX + S-GM | 10 | 10 |

[Single dose] ( ** administered once a day)
AMX: Amoxicillin
CLR: Clarithromycin
S-GM: Gentamicin-inserted smectite hybrid
PPI: Proton pump inhibitor

*H. pylori* IgG Antibody Titer in Blood
1) Confirmation of *H. pylori* Infection and Measurement Results for Group Configuration A *H. pylori* antibody was measured by ELISA and the mean and standard deviation were calculated, and as a result, the mean value of a non-infected group was measured as 0.04±0.01, and the mean value of an infected group was measured as 0.10±0.10. The *H. pylori* antibody was statistically significantly increased to 150.0% in the infected group compared to the non-infected group (p<0.05) (Table 6).

TABLE 6

| | *H. pylori* IgG test |
|---|---|
| Non-infected group | 0.04 ± 0.01 |
| infected group | 0.10 ± 0.10* |

*H. pylori* antibody IgG test values after 1 week of infection.
Data were expressed as mean ± standard deviation. Statistical analysis was performed with Sigma plot statistic.
*Comparison with non-infected group.
*p <0.05

2) Measurement Result of Final *H. pylori* Antibody IgG

As a result of calculating the mean and standard deviation by measuring a *H. pylori* antibody in the blood at autopsy, the *H. pylori* antibody was measured in a non-infected group (normal control group): 0.33±0.13, a negative control group as an infection control group: 0.63±0.29, Test group 1 (AMX+CLR+PPI administered group): 0.27±0.07, Test group 2 (AMX+S-GM+PPI administered group): 0.19±0.04, and Test group 3 (AMX+S-GM administered group): 0.22±0.06.

In the negative control group infected with *H. pylori*, an increase in *H. pylori* antibody was measured to 90.9% or more compared to the normal control group as the non-infected group without *H. pylori* infection, and thus, it was confirmed that *H. pylori* infection was maintained statistically significant (p<0.01). In Test group 1 (AMX+CLR+PPI administered group), as a positive control group, the *H. pylori* antibody was statistically significantly decreased to 57.1% compared to the negative control group (p<0.01). In Test group 2 (AMX+S-GM+PPI administered group) and Test group 3 (AMX+S-GM administered group) as test substance groups, the *H. pylori* antibodies were statistically significantly decreased to 69.8% and 65.1% compared to the negative control group, respectively (P<0.01). In Test group 2 and Test group 3 as test substance groups, compared to Test group 1 as the positive control group, the *H. pylori* antibodies were statistically significantly decreased to 29.6% and 18.5%, respectively, and in particular, the reduction effect of Test group 2 was excellent (p<0.01, p<0.05).

Gastric Histopathological Analysis Results

As a result of visual observation of the extracted gastric tissue after autopsy, no specific lesions were observed in the non-infected group (normal control group), the negative control group as the infection group, and all Test groups 1 to 3. As the histopathological result, the findings observed in the gastric tissue were scored for damage of the surface epithelium, inflammatory cell infiltration, and submucosal edema. For each item, it was classified as non-observed 0 point, Mild 0.5 point, and Moderate 1 point.

As a result, in the normal control group, it was observed that the damage of the surface epithelium was 0.10±0.21 point, the inflammatory cell infiltration was 0.15±0.24 point, and the submucosal edema was 0.10±0.32 point, and the total score was 0.35±0.41 point. In the negative control group, it was observed that the damage of the surface epithelium was 0.65±0.34 point, the inflammatory cell infiltration was 0.40±0.32 point, and the submucosal edema was 0.55±0.37 point, and the total score was 1.60±0.81 point. In Test group 1 (AMX+CLR+PPI administered group), it was observed that the damage of the surface epithelium was 0.30±0.42 point, the inflammatory cell infiltration was 0.40±0.46 point, and the submucosal edema was 0.60±0.46 point, and the total score was 1.30±1.14 point. In Test group 2 (AMX+S-GM+PPI administered group), it was observed that the damage of the surface epithelium was 0.30±0.35 point, the inflammatory cell infiltration was 0.15±0.24 point, and the submucosal edema was 0.35±0.34 point, and the total score was 0.80±0.79 point. In Test group 3 (AMX+S-GM+PPI administered group), it was observed that the damage of the surface epithelium was 0.60±0.39 point, the inflammatory cell infiltration was 0.40±0.46 point, and the submucosal edema was 0.65±0.41 point, and the total score was 1.65±1.11 point (Table 7).

Result of CLO Rapid Urease Test

A CLO rapid urease test was performed on the gastric tissue, and it was plotted to calculate the percentage of the number of positive samples to the total number of samples.

As a result, if a case with a moderate color (partially positive) was considered as an individual having a response to treatment, the cure rates were 50% for a standard treatment group, Test group 1 (AMX+CLR+PPI administered group), 70% for Test group 2 (AMX+S-GM+PPI administered group), and 10% for Test group 3 (AMX+S-GM administered group), and thus, Test group 2 showed the best cure rate (Table 8).

TABLE 7

| | | | Histopathological score | | | |
|---|---|---|---|---|---|---|
| | | | Damage of the surface epithelium | Inflammatory cell infiltration | Submucosal edema | Total Score |
| Normal control group | PBS | Distilled water | 0.10 ± 0.21 | 0.15 ± 0.24 | 0.10 ± 0.32 | 0.38 ± 0.41 |
| Negative control group | H. pylori | Distilled water | 0.65 ± 0.34** | 0.40 ± 0.32** | 0.55 ± 0.37** | 1.60 ± 0.81** |
| Test group 1 | | AMX + CLR + PPI | 0.30 ± 0.42** | 0.40 ± 0.46 | 0.60 ± 0.46 | 1.30 ± 1.14 |
| Test group 2 | | AMX + S-GM + PPI | 0.30 ± 0.35** | 0.15 ± 0.24** | 0.35 ± 0.34 | 0.80 ± 0.79** |
| Test group 3 | | AMX + S-GM | 0.60 ± 0.39 | 0.40 ± 0.46 | 0.65 ± 0.41 | 1.65 ± 1.11 |

Data were expressed as mean ± standard deviation.
Statistical analysis was performed with Sigma plot statistic.
*Comparison with non-infected group.
**p < 0.01,
comparison with negative control group,
p < 0.01

As a result of comparing the scores for the item of "damage of the surface epithelium" for each group, a statistically significant increase was observed in the negative control group compared to the normal control group (p<0.01), and only in Test Group 1 (AMX+CLR+PPI administered group) and Test group 3 (AMX+S-GM+PPI administered group), it was statistically significantly decreased to 53.8% and 53.8%, compared to the negative control group, respectively (Table 7).

As a result of comparing the scores for the item of "inflammatory cell infiltration" for each group, a statistically significant increase was observed in the negative control group compared to the normal control group (p<0.01), and only in Test group 2 (AMX+S-GM+PPI administered group), it was statistically significantly decreased to 62.5% compared to the negative control group (Table 7).

As a result of comparing the scores for the item of "submucosal edema" for each group, a statistically significant increase was observed in the negative control group compared to the normal control group (p<0.01), and no statistically significant difference was observed between the remaining groups (Table 7).

As a result of comparing the total scores obtained by summing the scores of the three histopathological findings (damage of the surface epithelium, inflammatory cell infiltration, and submucosal edema) for each group, a statistically significant increase was observed in the negative control group compared to the normal control group (p<0.01), and only in Test group 1 (AMX+S-GM+PPI administered group), it was statistically significantly decreased to 50.0% compared to the negative control group (Table 7).

TABLE 8

| | Disease induction | Test substance | Ratio positive | partially positive | negative |
|---|---|---|---|---|---|
| Normal control group | PBS | Distilled water | 0/10 | 0/10 | 10/10 |
| Negative control group | H. pylori | Distilled water | 10/10 | 0/10 | 0/10 |
| Test group 1 | | AMX + CLR + PPI | 5/10 | 0/10 | 5/10 |
| Test group 2 | | AMX + S-GM + PPI | 3/10 | 1/10 | 6/10 |
| Test group 3 | | AMX + S-GM | 9/10 | 0/10 | 1/10 |

Result of Experimental Example 7

Resistant Rate by Antibiotic

Clarithromycin showed a very high resistant rate of 29.8%, and had the highest resistant rate of 37.2% to levofloxacin, which was not widely used for eradicating *Helicobacter* in clinical practice. Therefore, it was judged that clarithromycin would not be suitable for use in preparing a clay mineral complex. As aminoglycoside-based antibiotics, which were a candidate antibiotic group to be used in the clay mineral complex, gentamicin and netilmicin showed relatively low MIC and resistant rates (2.78% and 1.43%, respectively) based on MIC 1 μg/mL and thus, the gentamicin and netilmicin were judged as a suitable candidate antibiotic group. However, tobramycin (TOB) had a resistant rate of 36.3%, and amikacin (AMK) also had a resistant rate of 61.3%, which were judged to be inappropriate as a candidate antibiotic group (FIG. 7). AMX: amoxicillin, CLR: clarithromycin, MTZ: metronidazole, TET: tetracyclin, LEV: levofloxacin. GM: gentamicin, NET: netilmicin, TOB: tobramycin, AMK: amikacin.

Eradicating Effect on Clarithromycin-Resistant Bacteria

An effect of eradicating clarithromycin-resistant *H. pylori* in vitro was evaluated. As a result of twice repeated tests, the gentamicin-smectite complex (S-GM) showed a clear zone around a disk. Therefore, it was confirmed that the gentamicin-smectite complex (S-GM) had an eradication activity on clarithromycin-resistant *H. pylori*. On the other hand, there was no clear zone around the clarithromycin (CLR) disk. The results of the twice repeated tests were the same, and each result was shown in FIGS. 8A and 8B. (FIGS. 8A and 8B: Top: CLR: Clarithromycin, Bottom: S-GM: Gentamicin-smectite complex).

Review of Experimental Results

In the present invention, the anti-*H. pylori* efficacy of S-GEN was evaluated in a mouse model. The experimental results of the present invention has proved a significantly improved antimicrobial effect of S-GEN to reduce a *H. pylori* load in mouse stomachs compared to those of other therapies, including a triple therapy which was a current world standard for *H. pylori* treatment.

The present inventors developed S-GEN and evaluated whether S-GEN was effective in the treatment of *H. pylori* infection. *H. pylori* mainly lived in a mucous layer adhering to the epithelial surface of the gastric mucosa. Therefore, for effective treatment, S-GEN needs to cross the mucous layer and remain on the gastric wall. In the present invention, S-GEN was well distributed on the gastric wall of the terminal, and the presence of 60.2% of S-GEN was observed, which indicated that S-GEN was effectively maintained up to 1 hour. This result suggests that S-GEN may be used for direct eradication of *H. pylori*.

In the results of *H. pylori* PCR and CLO tests with the gastric mucosa after treatment, Group 5 showed the highest cure rate (80%) among the treated groups. In addition, the CLO value in Group 5 was the lowest among the treated groups (0.6±1.3). The anti-*H. pylori* efficacy was evident in Group 5. In the case of the *H. pylori* PCR test with feces after treatment for *H. pylori* infection, negative results were continuously observed only in Group 5. Therefore, the excellent anti-*H. pylori* activity given by the S-GEN triple therapy may be explained as more lasting its direct eradicating effect and the eradicating effect by being applied for a longer time on the gastric mucosa compared to other therapies of conventional antibiotics.

Interestingly, S-GEN-treated mice had significantly reduced *H. pylori*-induced proinflammatory cytokines IL-8 and TNF-α as compared to mice which were infected with *H. pylori*, but untreated. IL-8 attracts neutrophils and promotes inflammation, and TNF-α induces gastrin secretion with IL-1β, which proposes roles of theses cytokines in *H. pylori*-induced hypergastrinaemia and inflammatory responses. The immune response to *H. pylori* contributes to the development of the disease. Therefore, as observed herein, a reduction in the proinflammatory response is expected to reduce the inflammatory response responsible for permanent tissue damage. After S-GEN treatment, better anti-*H. pylori* effect than those achieved with other therapies and early elimination of colonization could reduce gastric inflammation.

In the present invention, treatment with S-GEN did not affect the mouse body weight. The safety of smectite by oral administration was proved, and gentamicin was not absorbed through the gastric mucosa.

The present inventors have proved the strong antimicrobial activity of S-GEN against *H. pylori* and the long-term application effect of S-GEN on the gastric mucosa. S-GEN treatment reduced the bacterial burden in vivo compared to mice treated with a double or triple therapy including PPI or untreated mice. In addition to the direct eradicating effect, S-GEN has helped in reducing inflammatory responses by inhibiting production of proinflammatory cytokines.

In addition, it was confirmed that when S-GEN was administered with the β-lactam antibiotic and the gastric acid inhibitor, the eradicating effect of *Helicobacter pylori* was more significant than the eradicating effect when S-GEN was administered with only the β-lactam antibiotic.

In addition, the resistant rate of *H. pylori* to clarithromycin, which is an antibiotic widely used in clinical practice, is high as 29.8%, but S-GEN also has the eradication activity on clarithromycin-resistant *H. pylori*, and thus, it is judged that S-GEN is useful even for patients who do not have an eradicating effect on clarithromycin.

INDUSTRIAL AVAILABILITY

The present invention relates to a method for eradicating *Helicobacter pylori*, including a step of administering a complex of a non-absorbable antibiotic and a clay mineral or a composition including the same to a subject. Further, the present invention relates to a method for preventing or treating gastrointestinal diseases caused by *Helicobacter pylori*, including a step of administering a complex of a non-absorbable antibiotic and a clay mineral or a composition including the same to a subject. Further, the present invention relates to an orally administered pharmaceutical composition or kit for eradicating *Helicobacter pylori*, including a complex of a non-absorbable antibiotic and a clay mineral. The pharmaceutical composition and kit of the present invention may further include a β-lactam antibiotic and/or a gastric acid inhibitor.

[Sequence List Free Text]

SEQ ID NO: 1 is a base sequence of a sense primer for amplification of *H. pylori*-specific ureA and ureC.

SEQ ID NO: 2 is a base sequence of an antisense primer for amplification of *H. pylori*-specific ureA and ureC.

SEQ ID NO: 3 is a base sequence of a sense primer for amplification of GAPDH.

SEQ ID NO: 4 is a base sequence of an antisense primer for amplification of GAPDH.

The invention claimed is:

1. An orally administered pharmaceutical composition for eradicating clarithromycin-resistant *Helicobacter pylori*, comprising a β-lactam antibiotic, and a gastric acid inhibitor, and a complex of a non-absorbable antibiotic with clay mineral,
   wherein the non-absorbable antibiotic is selected from the group consisting of gentamicin and netilmicin at an effective amount that eradicates the clarithromycin-resistant *Helicobacter pylori* and decreases damage of the surface epithelium, inflammatory cell infiltration, and/or submucosal edema, and
   wherein the clay mineral is selected from the group consisting of montmorillonite, bentonite, beidellite, nontronite, saponite, and hectorite.

2. The pharmaceutical composition of claim 1, wherein the pharmaceutical composition has an urease inhibitory activity.

3. The pharmaceutical composition of claim 1, wherein the pharmaceutical composition is for treating gastrointestinal diseases caused by *Helicobacter pylori* bacteria.

4. An orally administered kit for eradicating clarithromycin-resistant *Helicobacter pylori*, comprising a β-lactam antibiotic, a gastric acid inhibitor, and a complex of a non-absorbable antibiotic and a clay mineral,
   wherein the non-absorbable antibiotic is selected from the group consisting of gentamicin and netilmicin at an effective amount that eradicates the clarithromycin-resistant *Helicobacter pylori* and decreases damage of the surface epithelium, inflammatory cell infiltration, and/or submucosal edema, and
   wherein the clay mineral is selected from the group consisting of montmorillonite, bentonite, beidellite, nontronite, saponite, and hectorite.

* * * * *